US00PP23747P3

(12) United States Plant Patent
Dirr et al.

(10) Patent No.: US PP23,747 P3
(45) Date of Patent: Jul. 16, 2013

(54) ***BERBERIS THUNBERGII* PLANT NAMED 'DAYBREAK'**

(50) Latin Name: *Berberis thunbergii*
Varietal Denomination: Daybreak

(75) Inventors: Michael A. Dirr, Bogart, GA (US); Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 83 days.

(21) Appl. No.: 13/373,361

(22) Filed: Nov. 10, 2011

(65) Prior Publication Data

US 2013/0125274 P1 May 16, 2013

(51) Int. Cl.
*A01H 5/00* (2006.01)

(52) U.S. Cl.
USPC ..... Plt./241

(58) Field of Classification Search
USPC ..... Plt./241
See application file for complete search history.

(56) References Cited

U.S. PATENT DOCUMENTS

PP8,215 P 4/1993 Moretti
PP20,602 P2 12/2009 Talago

OTHER PUBLICATIONS

Plant Introductions, Inc. webpage, (downloaded Nov. 3, 2011) "*Berberis thunbergii*", http://www.plantintroductions.com/berberis-selection.html Plant Introductions, Inc., 2 pages.
*Berberis thunbergii* 'Daybreak' Catalog Page (distributed at a trade show Jan. 5, 2011) Plant Introductions, Inc., 1 page.

*Primary Examiner* — Annette Para
(74) *Attorney, Agent, or Firm* — Lathrop & Gage LLP

(57) ABSTRACT

A new and distinct cultivar of *Berberis thunbergii* plant named 'Daybreak', characterized by its compact, mounding growth habit, small, lustrous, medium green foliage that turns bright yellow in fall, reddish-orange flowers produced in abundance from spring to fall, greenish-tan to reddish-green fruits, and root/crown cold hardiness to USDA Hardiness Zone 7.

3 Drawing Sheets

Genus and species of plant claimed: *Berberis thunbergii.*

Variety denomination: 'Daybreak'.

BACKGROUND OF THE INVENTION

The present invention relates to a new and distinct cultivar of *Berberis thunbergii,* a member of the Berberidaceae family, hereinafter referred to by its cultivar name 'Daybreak'. 'Daybreak' is grown primarily as an ornamental for landscape use.

'Daybreak' originated from an open-pollination of *Berberis thunbergii* 'Bogozam' (U.S. Plant Pat. No. 8,215) and was selected from the progeny of this pollination by continued evaluation for growth habit and foliage characteristics.

'Daybreak' has been asexually reproduced by softwood cuttings since 2008 in Watkinsville, Ga. The characteristics of 'Daybreak' have been stable and reproduced true-to-type in successive vegetative generations.

SUMMARY OF THE INVENTION

'Daybreak' has not been observed under all possible environmental conditions. The phenotype may vary somewhat with changes in light, temperature, soil and rainfall without, however, any variance in genotype.

The following traits have been observed and represent the characteristics of 'Daybreak'. In combination these characteristics distinguish 'Daybreak' from all other varieties in commerce known to the inventor. 1) Compact, mounding growth habit. 2) Foliage that emerges orange in spring, changes to yellow-green in summer, and turns orange-red in fall. 3) Resistance of foliage to sun-scald/photobleaching.

'Daybreak' is distinguished from its female parent 'Bogozam' by its vigor, growth habit, and foliage characteristics. 'Daybreak' has a more vigorous, compact, mounding growth habit, whereas 'Bogozam' has a less vigorous spreading growth habit. 'Daybreak' has foliage that emerges orange in spring and turns orange-red in fall, whereas 'Bogozam' has foliage that emerges yellow-green in spring and turns yellow in fall. There are no other cultivars of *Berberis thunbergii* with this combination of characteristics known to the inventor.

Plants of 'Daybreak' can be compared to plants of the cultivar 'Talago' (U.S. Plant Pat. No. 20,602). However, in side-by-side comparisons conducted in Watkinsville, Ga., plants of 'Daybreak' differed from plants of 'Talago' in the following characteristics: 1. Plants of 'Daybreak' had a compact, mounding growth habit, whereas plants of 'Talago' had a compact, rounded growth habit and had a tendency to become loose and open-up in the middle; 2. Plants of 'Daybreak' had foliage that emerged orange in spring and turned orange-red in fall, whereas plants of 'Talago' had foliage that emerged red in spring and turned red in fall; 3. Plants of 'Daybreak' had foliage that was more resistant to sun-scald/photobleaching than plants of 'Talago'.

BRIEF DESCRIPTION OF THE DRAWINGS

The accompanying illustrations show characteristics of 'Daybreak' in photographs as true to color as is reasonably possible to make in illustrations of this nature. Colors in the photographs may differ slightly from the color values cited in the detailed botanical description which accurately describe the colors of the new *Berberis.*

DETAILED DESCRIPTION

Figure 1:
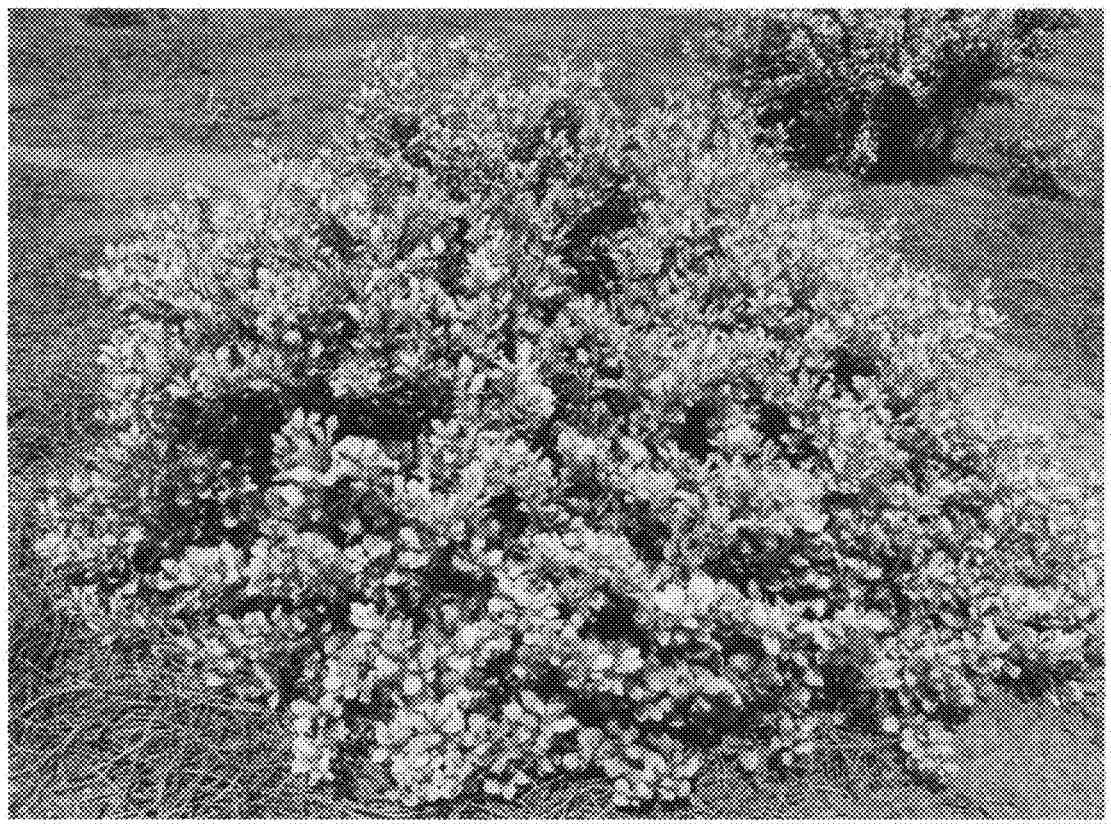
FIG. 1 shows the overall appearance of a mature plant of 'Daybreak'.
Figure 2:
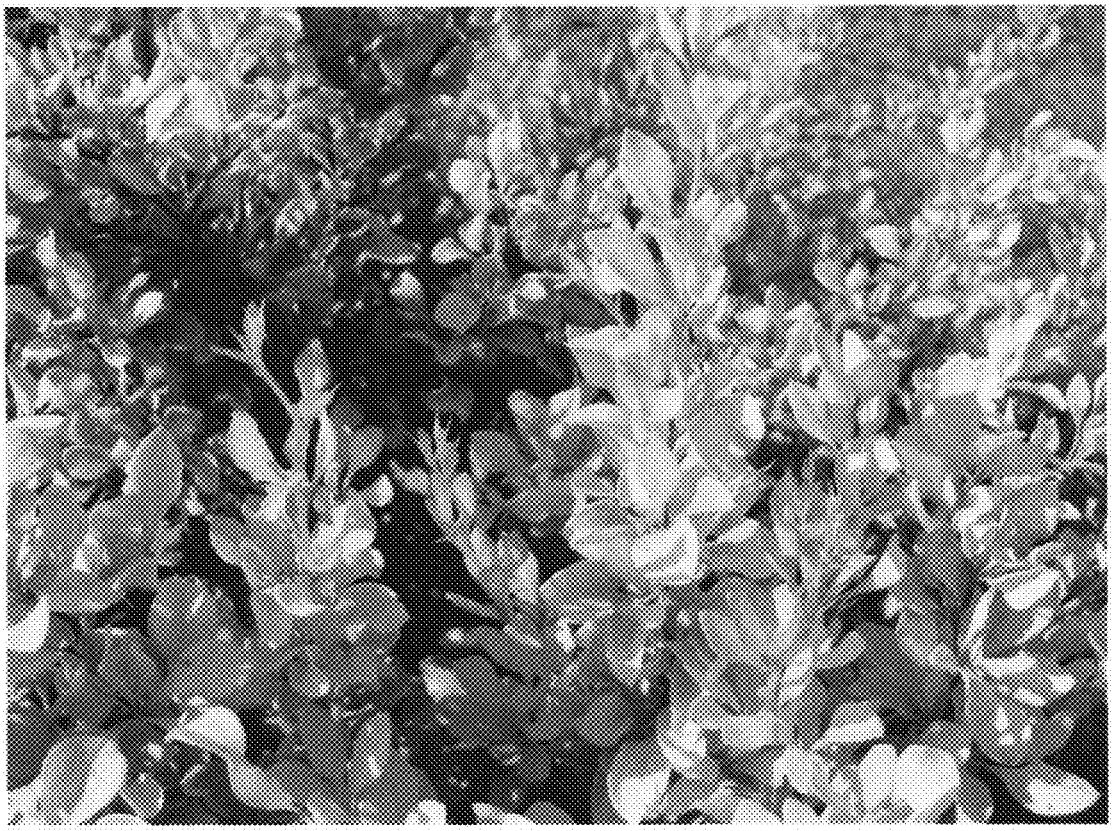
FIG. 2 shows a close-up of the new growth and mature foliage of 'Daybreak'.
Figure 3:
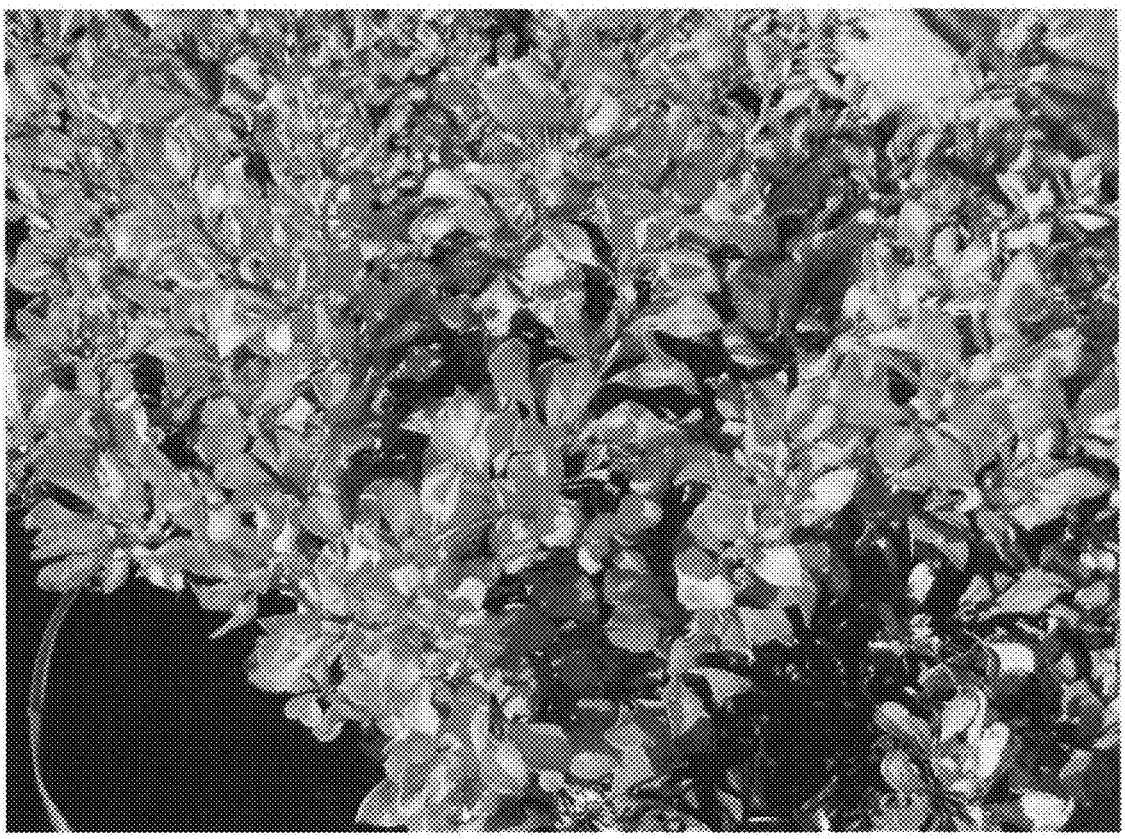
FIG. 3 shows a close-up of the fall color of 'Daybreak'

In the following description, color references are made to The Royal Horticultural Society Colour Chart, 2001 Edition, except where general terms of ordinary dictionary significance are used. Plants used for the description were grown in 11.8 L containers in full sun under outdoor conditions in a nursery in Watkinsville, Ga. Plants were approximately 2½ years old when the description was recorded.

Botanical classification: 'Daybreak' is a cultivar of *Berberis thunbergii.*

Parentage: The current variety is a progeny from an open-pollination of *Berberis thunbergii* 'Bogozam' (U.S. Plant Pat. No. 8,215).

Propagation: Vegetatively by stem cuttings.

Plant description: The claimed variety is a freely branching, compact mounding deciduous shrub.

*Root description.*—Numerous, fibrous, and well-branched.

*Plant size.*—The original plant, now about three-years-old in the ground, is about 33 cm high from the soil to the top of the foliage and about 56 cm wide. First year stems have a diameter of about 2 mm. Shape: round. Texture: glabrous, no pubescence, no exfoliation.

*First year stem color.*—154B when young, maturing to 164B.

*Internode length.*—About 5 mm. Second year and older stems have a diameter of about 3 mm or more. Shape: round.

*Second year and older stem color.*—199D with striations that are 200A in color.

*Trunk diameter.*—About 1.5 cm in diameter at the soil level and the color is 199D with striations that are 200A in color. All stems and the trunk have approximately 3 spines per cm of length. The spines are about 7 mm long and less than 1 mm in width. The color of the spines is 154B on new growth, maturing to 164B, and finally 200A on older stems and the trunk. The spines are somewhat flexible when young, becoming woody as they mature.

Vegetative bud description:

*Arrangement.*—Alternate, solitary, sessile borne on short (1 to 2 mm spurs).

*Shape.*—Ovoid.

*Size.*—About 2 mm in length, about 1 mm in width.

*Color.*—154A when young maturing to 200A.

Foliage description:

*Arrangement.*—Alternate, simple, borne in clusters along the stems.

*Leaf size.*—About 1.5 cm long and about 8 mm wide.

*Shape.*—Spatulate-oblong. Apex: obtuse, with a short spine about 1 mm long at the tip. Base: attenuate. Margin: entire.

*Texture of upper and lower leaf surfaces.*—Glabrous.

*Color of emerging leaves.*—150A on the upper surface with a margin that is 176C and the lower surface is 150C. Color of mature leaves: 150A on the upper surface and 150C on the lower surface. Lower mature leaves that are shaded by the upper foliage: 137A on the upper surface and 138B on the lower surface. Fall color on upper and lower surfaces: N163C, 171B, 179A, or any combination of these colors.

*Petiole length.*—About 2 mm. Petiole diameter: about 1 mm. Petiole texture: glabrous. Petiole color: 176C on the upper surface and 150C on the lower surface.

Flower description: To date, flowers have not been observed on 'Daybreak'.

Fruit: Top date, fruit has not been observed on 'Daybreak'.

Disease/pest resistance: No specific pest or disease resistance/susceptibility has been observed.

We claim:

1. A new and distinct *Berberis thunbergii* plant named 'Daybreak', substantially as illustrated and described herein.

* * * * *